United States Patent
Stayman (10) Patent No.: US 7,852,980 B2
(45) Date of Patent: Dec. 14, 2010

(54) COMPUTED TOMOGRAPHY WITH RESOLUTION RECOVERY

(75) Inventor: Joseph W. Stayman, Ann Arbor, MI (US)

(73) Assignee: Xoran Technologies, Inc., Ann Arbor, MI (US)

( * ) Notice: Subject to any disclaimer, the term of this patent is extended or adjusted under 35 U.S.C. 154(b) by 0 days.

(21) Appl. No.: 12/262,600

(22) Filed: Oct. 31, 2008

(65) Prior Publication Data

US 2009/0110141 A1  Apr. 30, 2009

Related U.S. Application Data

(60) Provisional application No. 60/984,093, filed on Oct. 31, 2007.

(51) Int. Cl.
  *G01N 23/04* (2006.01)
(52) U.S. Cl. .................. 378/19; 378/62; 378/901
(58) Field of Classification Search ............ 378/19, 378/62, 210, 901; 382/131, 255, 275
See application file for complete search history.

(56) References Cited

U.S. PATENT DOCUMENTS

| | | | |
|---|---|---|---|
| 4,549,265 A | | 10/1985 | Deckers et al. |
| 4,791,934 A | | 12/1988 | Brunnett |
| 4,991,189 A | * | 2/1991 | Boomgaarden et al. ......... 378/4 |
| 5,131,021 A | * | 7/1992 | Gard et al. ................... 378/19 |
| 5,265,142 A | | 11/1993 | Hsieh |
| 5,430,783 A | | 7/1995 | Hu et al. |
| 5,469,429 A | * | 11/1995 | Yamazaki et al. ............. 378/19 |
| 5,473,656 A | * | 12/1995 | Hsieh et al. ..................... 378/4 |
| 5,818,896 A | | 10/1998 | Hsieh |
| 5,864,598 A | | 1/1999 | Hsieh et al. |
| 5,907,593 A | | 5/1999 | Hsieh et al. |
| 5,933,471 A | | 8/1999 | Kalvin |
| 5,999,587 A | | 12/1999 | Ning et al. |
| 6,014,420 A | * | 1/2000 | Ooi ............................... 378/19 |

(Continued)

OTHER PUBLICATIONS

Kamm, Julie et al., Kronecker Product and SVD Approximations for Separable Spatially Variant Blurs, Apr. 1998, Dept. of Mathematics, Southern Methodist University, pp. 1-13.*

(Continued)

*Primary Examiner*—Edward J Glick
*Assistant Examiner*—Anastasia Midkiff
(74) *Attorney, Agent, or Firm*—Brinks Hofer Gilson & Lione (57) ABSTRACT

A system and method for recovering resolution in an x-ray computed tomography system. The system includes an x-ray source, a two-dimensional sensing array, and a controller. The x-ray source projects an x-ray beam towards subject. The x-ray source includes an anode and a cathode, where the anode has a target for directing the x-ray beam. A two-dimensional sensing array receives an x-ray beam through the subject to generate an image. The target of the anode causes a shift variant blur of the x-ray beam received by the sensing array due to the angle between the target and the sensing array. The controller is in communication with the sensing array to control acquisition and processing of the image. The controller is configured to adjust for the shift variant blur of the x-ray beam.

13 Claims, 6 Drawing Sheets

U.S. PATENT DOCUMENTS 6,094,469 A * 7/2000 Dobbs et al. .................. 378/19
6,256,404 B1 7/2001 Gordon et al.
6,411,670 B1 6/2002 Besson

OTHER PUBLICATIONS

J. Stayman, J. Alspaugh, M. Goodsitt, E. Christodoulou, "xCAT: A dedicated, portable, head and neck volume CT scanner," *49th Annual AAPM Meeting*, Jul. 22-26, 2007.

G. Zeng, G. Gullberg, B. Tsui et al., "Three-dimensional iterative reconstruction algorithms with attenuation and geometric point response correction," *IEEE Trans Nuc Sci.* 38:693:702, 1991.

Z. Liang, T. Turkington, D. Guilland et al., "Simultaneous compensation for attenuation, scatter, and detector response for SPECT reconstruction in three dimensions," *Phys. Med. Biol.* vol. 37, pp. 587-603, 1992.

H. Erdogan, J. Fessler, "Ordered subsets algorithms for transmission tomography," *Phys. Med. Biol.* 44(11):2835-51, Nov. 1999.

* cited by examiner

COMPUTED TOMOGRAPHY WITH RESOLUTION RECOVERY

CROSS-REFERENCE TO RELATED APPLICATIONS

The present invention claims priority to U.S. Provisional Ser. No. 60/984,093, filed Oct. 31, 2007, entitled "Computed Tomography with Resolution Recovery", which is herein incorporated by reference.

BACKGROUND

1. Field of the Invention

The present invention generally relates to a system and method for recovering resolution in an x-ray computed tomography system.

2. Description of Related Art

In a typical x-ray computed tomography system, an x-ray source projects an x-ray beam through an object and onto a detector. The x-ray source is generally thought of as a point source. However, the focal spot of the x-ray source is actually projected onto a surface and, therefore, has a different apparent size and shape depending on the perspective angle relative to the surface. The projection of an extended focal spot onto the detector may result in significant blur. This system blur is shift variant and depends on the exact geometry of the computed tomography system and the shape of the focal spot. Typically this form of system blur is ignored and mitigated by construction of an x-ray source with a smaller focal spot. This places extraordinary demands on x-ray source design since energy is concentrated on smaller areas of the x-ray target. Such requirements have led to large rotating anode sources with sophisticated mechanisms for removing excess heat. With the simultaneous drive for ever smaller reconstructed voxel sizes and physically smaller computed tomography systems, it may be helpful to approach this problem from both the source design and the data processing sides.

In view of the above, it is apparent that there exists a need for a system and method for recovering resolution in an x-ray computed tomography system.

SUMMARY

In satisfying the above need, as well as overcoming the enumerated drawbacks and other limitations of the related art, the present invention provides a system and method for recovering resolution in an x-ray computed tomography system.

The system includes an x-ray source, a two-dimensional sensing array, and a controller. The x-ray source projects an x-ray beam towards subject. The x-ray source includes an anode and a cathode, where the anode has a target where the x-ray beam is generated. A two-dimensional sensing array receives an x-ray beam through the subject to generate an image. The target of the anode causes a shift variant blur of the x-ray beam received by the sensing array due to the angle between the target and the sensing array. The controller is in communication with the sensing array to control acquisition and processing of the image. The controller is configured to adjust for the shift variant blur of the x-ray beam.

In another aspect of the invention, the controller pre-computes a model of the shift variant blur based on the location, orientation, and size of the target. For example, the angle between the target and the sensing array may be used to generate the model. Further, the controller may generate a matrix corresponding to the system model and use the model of the shift variant blur within a model-based reconstruction approach to mitigate blur and improve special resolution.

Further objects, features and advantages of this invention will become readily apparent to persons skilled in the art after a review of the following description, with reference to the drawings and claims that are appended to and form a part of this specification.

DETAILED DESCRIPTION

Figure 1:
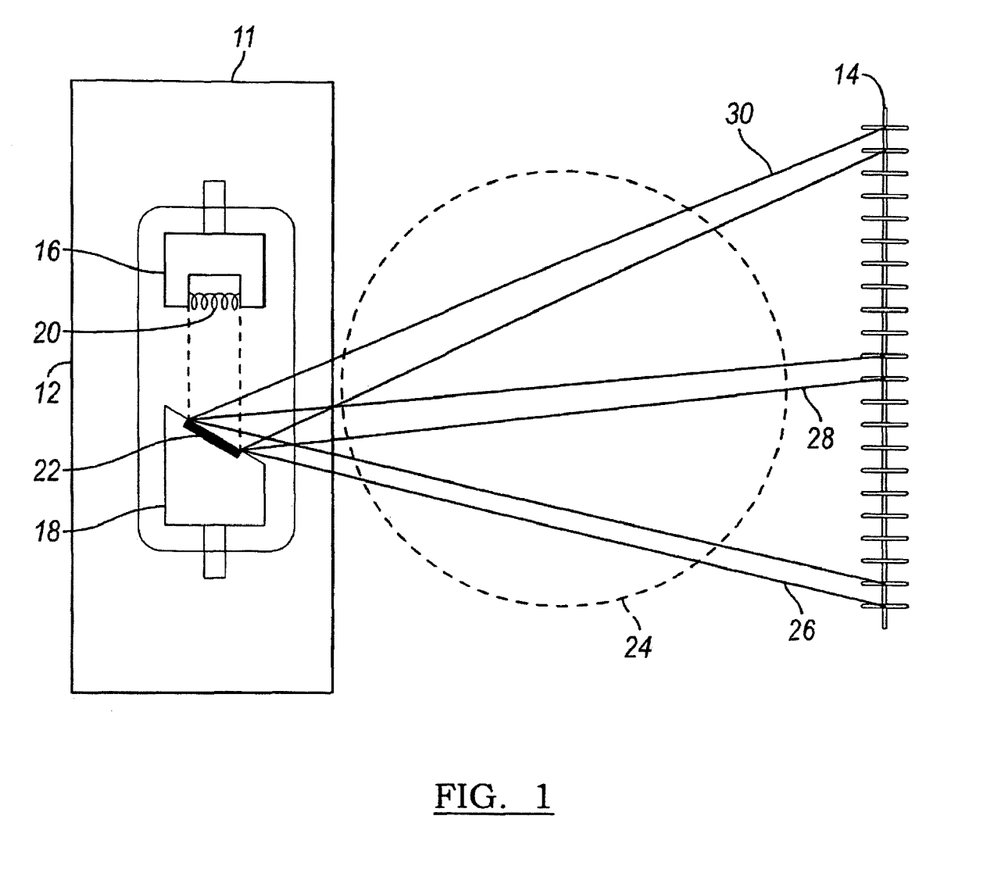
FIG. 1 is a system illustrating resolution recovery for a x-ray computed tomography system.

An x-ray computed tomography system illustrating shift variant blur is provided in FIG. 1. The system 10 contains an x-ray source 11 and a detector 14. The x-ray source 11 includes an x-ray tube 12 with a cathode 16 and an anode 18. The cathode 16 has a filament 20, such as a linear filament. X-rays are generated as electrons jump across the x-ray tube 12 from the filament 20 to a target 22 on the anode 18 of the x-ray tube 12. The filament 20 forms an extended line source on the target 22. However, the target 22 is angled so that there is a relatively oblique projection of the line source onto the detector 14. The detector 14 may be a pixilated detector, such as linear array detector or a two-dimensional detector array, for example an amorphous silicon flat panel (coupled with a scintillation crystal), a traditional multi row computed tomography detector, or other similar imaging detectors.

The x-rays are projected from the x-ray source 11 through the object 24 and onto the detector 14. Despite the oblique angle between the target 22 and the detector 14, there is obvious shift-variance in the x-ray beam width that connects the line source with individual detector elements. For example, the apparent width of the focal spot along the most oblique x-ray beam 26 will be the smallest. While the x-ray beam 28 will have a greater apparent width and the x-ray beam 30, most normal to the target 22, will have the greatest apparent width. The shift-variance of the blur in this system increases for 1) longer line lengths on the target; 2) increased fan/cone angles; and 3) detector elements mismatched with spot size (i.e.: much smaller detector elements).

All three of these conditions are present in many flat-panel based cone-beam computed tomography systems, which are rapidly gaining popularity due to their relative physical compactness and high isotropic spatial resolution. Flat panel systems have wide-area detectors (e.g.: up to 30×40 cm) and very small pixels (~100 μm). Flat-panel-based systems can be designed very compactly using relatively short source-detector distances and smaller, fixed anode sources (which tend to have larger focal spots than their rotating anode counterparts).

Figure 2:
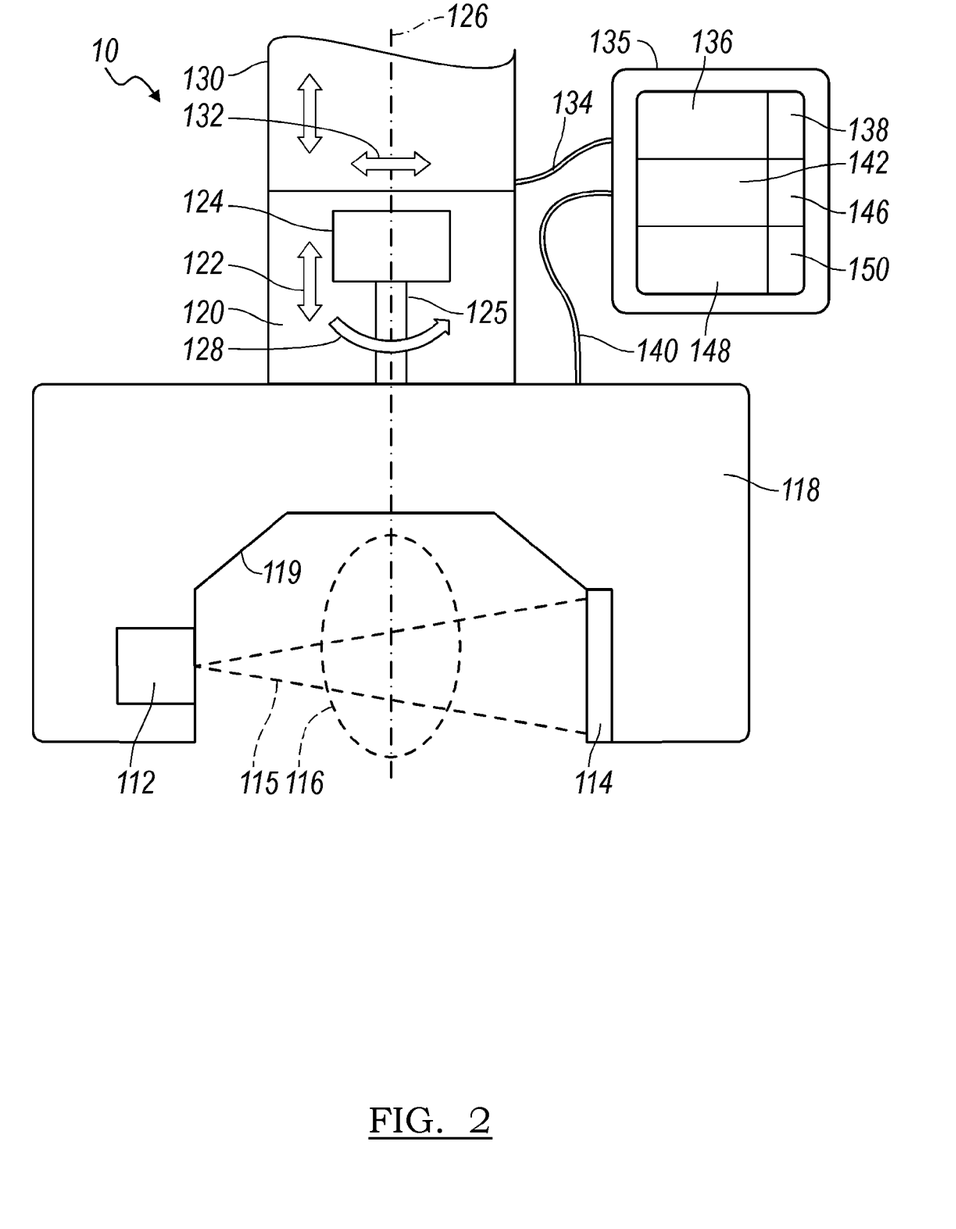
FIG. 2 is a schematic view of a system for performing computed tomography.

Referring now to FIG. 2, the flat panel system 10 includes an x-ray source 112 and a detector 114. The x-ray source 112 projects x-rays, denoted by reference number 115 through an object 116 and toward the detector 114. The detector 114, may be a two-dimensional detector array, such as an amorphous silicon flat panel (coupled with a scintillation crystal), a traditional multi row computed tomography detector, or other similar imaging detectors. The object 116 may for example, be the head of a patient and the system 110 may be configured to image a sinus cavity within the patient. The x-ray source 112 and the detector 114 may be mounted to a structure 118. The structure 118 maintains the position and orientation of the x-ray source 112 with respect to the detector 114. The structure 118 includes a recess 119 that allows various objects, for example, a patient's head to be located between the x-ray source 112 and the detector 114.

Figure 3:
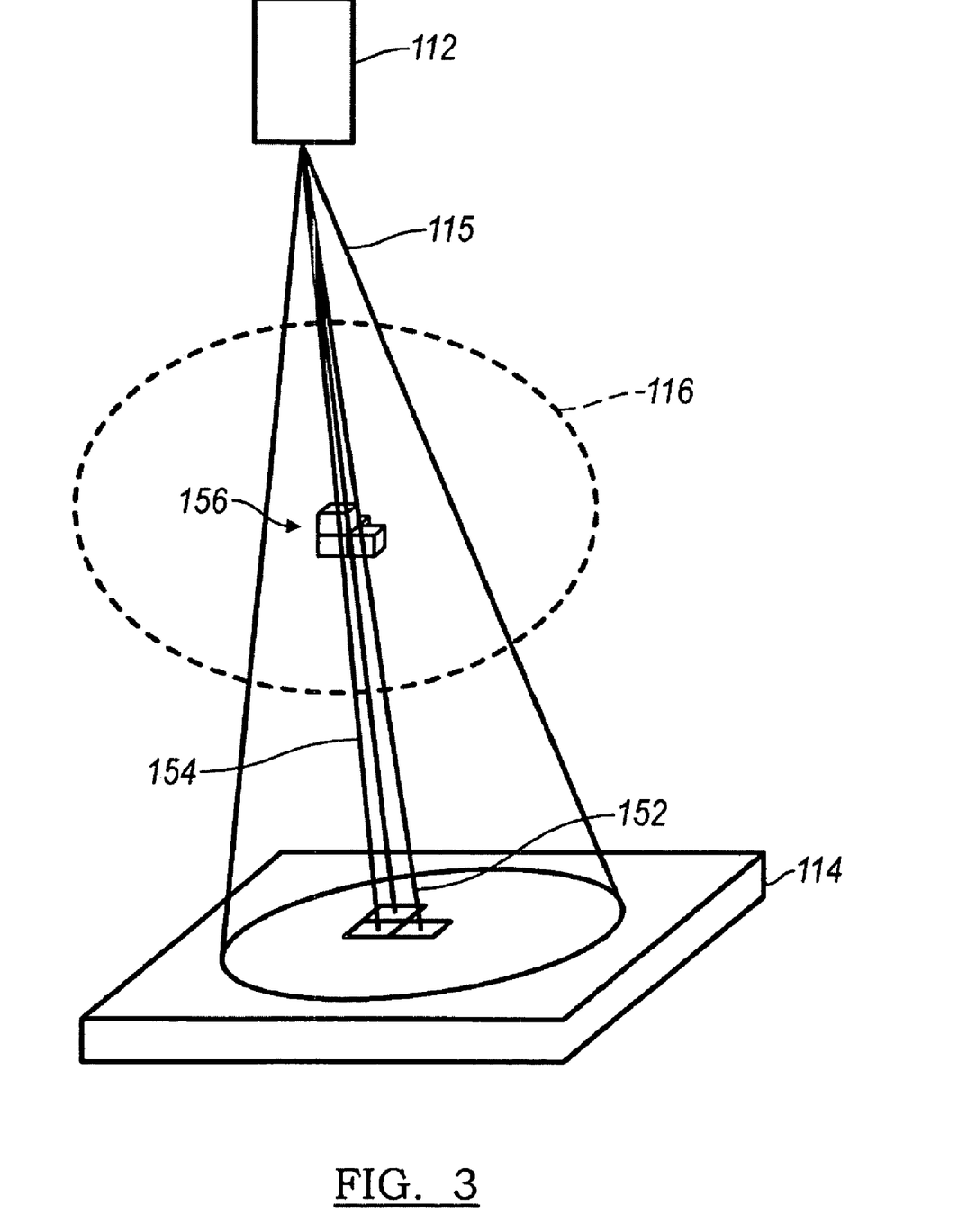
FIG. 3 is a perspective view of an x-ray source and detector.
Figure 4:
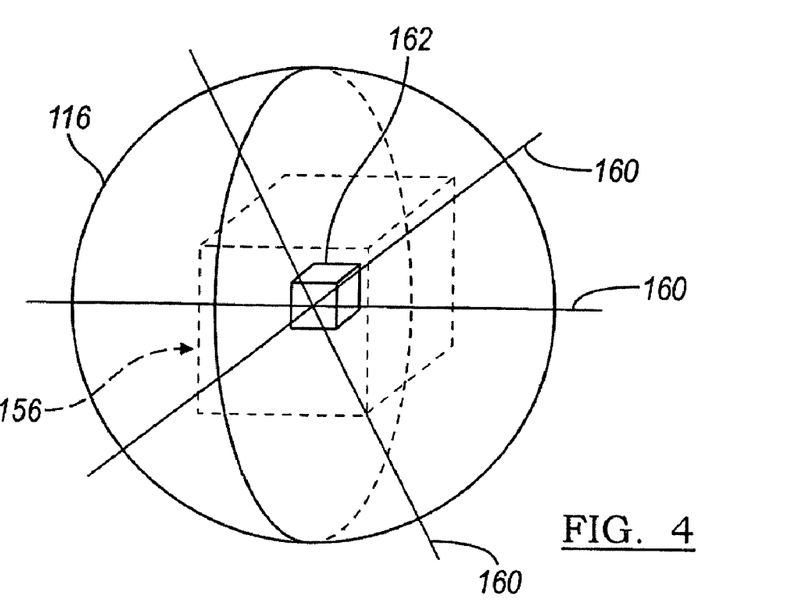
FIG. 4 is a perspective view of x-ray paths projected through a voxel.
Figure 5:
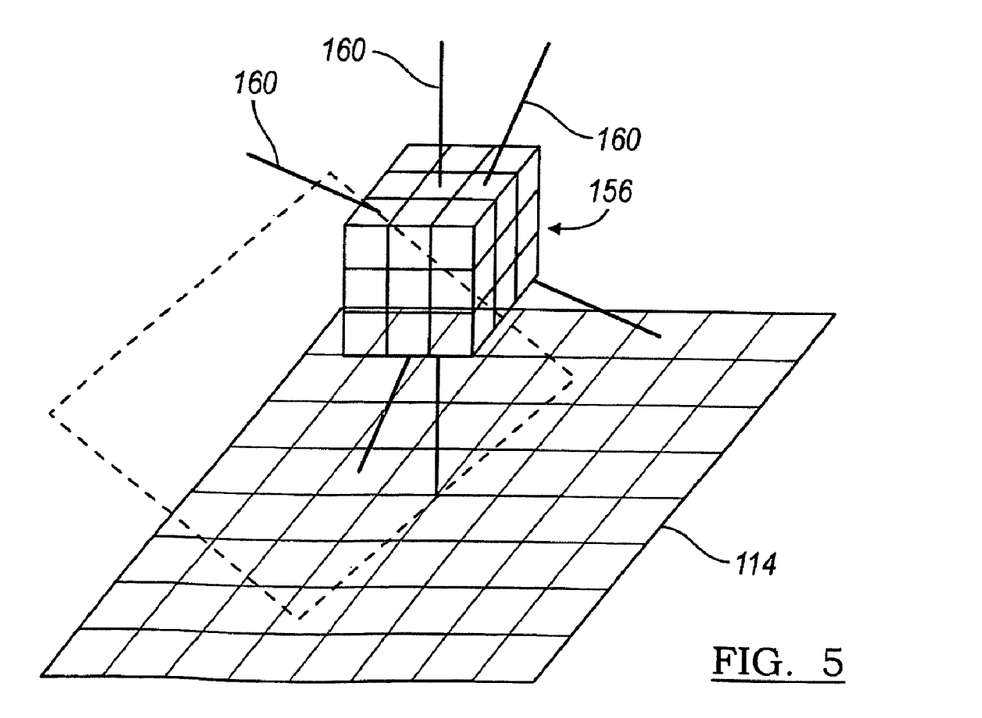
FIG. 5 is a perspective view of x-ray paths and combinations of voxels through which the x-ray paths pass.

The structure 118 is connected to a number of motion control devices configured to manipulate the position of the x-ray source 112 and detector 114 relative to the object 116. The x-ray beam is projected along each path to the detector 114. Each path generates a different intensity on the detector 114 based on the density of the object along that path, as shown in FIG. 3. As such, the intensity at each pixel 152 in the detector 114 corresponds to an accumulated density at each point along the line representing the x-ray path 154. Therefore, it is helpful to represent the object 116 as a model that is made up of small cube-type elements called voxels 156. The intensity seen at the two-dimensional detector 114 is a function of the density accumulation through each voxel 156 that the x-ray path 154 travels through. To calculate the density at a particular voxel 162, a number of x-ray path lines 160 through each voxel 156 may be utilized to isolate the density contribution for that particular voxel 162 as shown in FIG. 4 and FIG. 5. This serves as the basis for various computed tomography systems and many methods and adaptations are well known in the art.

Referring again to FIG. 2, the motion control devices described above may manipulate the position and orientation of the structure 118, thus the x-ray source 112 and detector 114, with regard to the object 116. As such, the system includes a linear gantry 120 configured to translate the structure 118 longitudinally along an axis 126, as denoted by arrow 122. Similarly, a second gantry 130 may be configured to translate the structure 118 laterally with respect to the axis 126, as denoted by arrow 132. As such, gantry 120 and gantry 130 may be oriented with their axis of translation perpendicular to one another providing a simple two-dimensional translation function between the gantries 120, 130. Further, a rotational stage 124 may be provided and connected to the structure 118 through a shaft 125. As such, the rotational stage 124 may be configured to rotate the structure 118 about the axis 126, as denoted by arrow 128.

The motion devices 120, 124, 130 are connected to a controller 135, as denoted by line 134. The connection may be through a cable or a wireless connection, or other standard means of system communication. The motion devices 120, 124, 130 are in communication with a motion control processor 136 of the controller 135. The motion control processor 136 generates electrical control signals to manipulate the motors of each of the motion control devices 120, 124, 130. In addition, the x-ray source 112 and the detector 114 are in communication with the controller 135, as denoted by line 140. As such, the detector 114 is in communication with an image acquisition and processing module 142. The image acquisition and processing module 142 receives data from the detector 114 and calculates the density for each voxel 156.

The density for each voxel 156 is calculated by storing the intensity projection for multiple x-ray path lines 160 through the object 116, as can be seen from FIG. 5. As described above, each x-ray path line 160 includes a different combination of voxels 154. The density of the object 116 within each voxel 156 may be isolated by solving each voxel's contribution to the accumulated density along each x-ray path line 160. Since the total density along each x-ray path 160 is known from the pixel intensity, the unknown voxel densities can be solved for utilizing the series of equations representing the voxel combinations along each x-ray path 160. In addition, the image processing module 142 may account for any difference in intensity response for each pixel 152 of the detector 114 in reconstructing each voxel 156 in the model. As such, the intensity profile or image for each position may be stored in memory 146. In addition, the memory 146 may also store the resulting density at each voxel and the relationship between each pixel on the detector 114. The relationship between the intensity response for each pixel on the detector 114 may be stored as parameters of an equation or in a look-up table format. Note that multiple x-ray paths are recorded at each position of the structure (i.e., one for each pixel on the detector).

The image processing module 142 may also implement a method for recovering the resolution lost as a result of this shift-variant blur. A model may be used where the detector response function is modeled and used as part of a likelihood-based objective function. A model based reconstruction allows the system to recover resolution that would be lost when traditional direct approaches (e.g.: filtered backprojection) are applied.

To adjust for the shift variant blur, the following measurement model is adopted for the system geometry. The model relates attenuation values in the object to measurement values using Beer's law and the ith mean measurements is defined as $$\bar{y}_i(\mu) = b_i e^{-[A\mu]_i} + r_i,$$

where $\mu$ denotes the vector of attenuation values in the image volume, i is the index for detector elements (pixels), $b_i$ denotes the mean value of the detector when no object is present (i.e. the blank scan), $r_i$ represents the (presumed known) contribution of scatter, and A is a matrix that represent the discretized projection operator. The projection operator is the mathematical embodiment of the geometry of each individual x-ray path to pixel relationship including the variations between x-ray paths based on angle, size of the line on the target, and the shape of the line on the target. Thus, $$[A\mu]_i = \sum_i a_{ij} \mu_j.$$

In a typical system $a_{ij}$ is defined as a straight line or strips of equal width. However, the system described herein has a more accurate system model that includes the shift variant detector responses. The system explicitly model the shift-variant detector response by computing the $a_{ij}$ terms according to the specific source and detector geometry—namely, the angle between the pixel and the line on the target, the size of the line, the shape of the line, and the shape of the detector element. Generally, in two-dimensions, with an extended line source and an extended square detector, the detector responses have a largely quadrilateral support (though the intensity may fluctuate along the length of the "line of response"). (The model may be extended to its 3-dimensional form as well.)

When the measurements are dominated by photon noise, a Poisson noise model is appropriate. However, other noise models like Gaussian, or mixed Poisson and Gaussian noise models could also be adopted based on the detector noise characteristics. For a Poisson noise model, a log-likelihood function may be written for estimation as $$L(\mu) = \sum_i h_i([A\mu]_i)$$

$$h_i(l) = y_i \log(b_i e^l + r_i) - (b_i e^l + r_i)$$

and the following likelihood-based objective may be solved to obtain a reconstruction $$\hat{\mu} = \arg\max_{\mu \geq 0} L(\mu).$$

Implementing another noise model may change the likelihood function, however, many noise models including but not limited to those mentioned above may be readily supported within this framework.

While there are many ways to maximize the above objective, a separable paraboloidal surrogates approach may be particularly useful. This approach can be used in both ordered-subsets and traditional variants. The system may use pre-computation of the so-called "fast denominator." The system can apply a configurable number of iterations based on the desired resolution and noise properties. The system may also be configured to obtain the fully-converged solution therefore the analysis may be focused on the convergent non-ordered subsets variant with many iterations (i.e.: 500 iterations).

As such, the contribution of shift variant blur for each pixel 152 may be modeled into a matrix. Further, the matrix may be integrated within the projection operation A to process the image generated by the detector 114.

An important factor to resolution recovery using iterative techniques is accurate modeling of the projection physics. Therefore, the system utilizes a fan-beam geometry allowing the system matrix to be pre-computed. Although, the system matrix may also be computed in real time to address memory constraints. To compute the values of A, a finite integration approach is used where individual line integrals are traced from a sampling of source points to a sampling of detector points (for each pixel). In other words, individual line integrals from evenly spaced points on the source to evenly spaced points on a detector pixel are traced and the sum of each line length through a voxel form that voxel's contribution to the ray sum. The finite integration approach may be a preferred method for accuracy, however more efficient approaches may be used to mitigate the blur, as well. For example, individual extremes at each end of the source and detector may be considered to estimate the blur contribution for the middle of the field.

To simplify the calculations, computed tomography systems with fourfold symmetry may be considered, requiring only 90 degrees worth of projection angles to be stored. The remaining 270 degrees may be formed using simple 90 degree rotations that do not necessitate any interpolation.

In addition, the controller 135 may include a display and planning module 148 that determines the series of positions and orientations of the structure 118 that will be necessary for constructing the model of the object 116. Such position planning may be stored in the memory 150 and transferred to or accessed by memory 138 of the motion control module 136. In addition, the planning and display module 148 may access or transfer the voxel model information from memory 150 to memory 146 of the image processing module 142.

A test of the above described system was performed. The model used in this investigation used the following geometry and system parameters. The source detector distance was 40 cm with the source placed perpendicularly to the detector center. The center of rotation was centered midway between source and detector. The detector contained 600 pixels (0.254 mm wide) sampled on a line (like a single row of flat-panel detector). The focal spot on the source was linear with a 3 mm length and the target was at a 15 degree angle. Projections were computed for 512 angles over 360 degrees. System matrix values were formed using finite integration with 10 source points and 10 detector points (i.e.: 100 line integrals per detector pixel).

Figure 6:
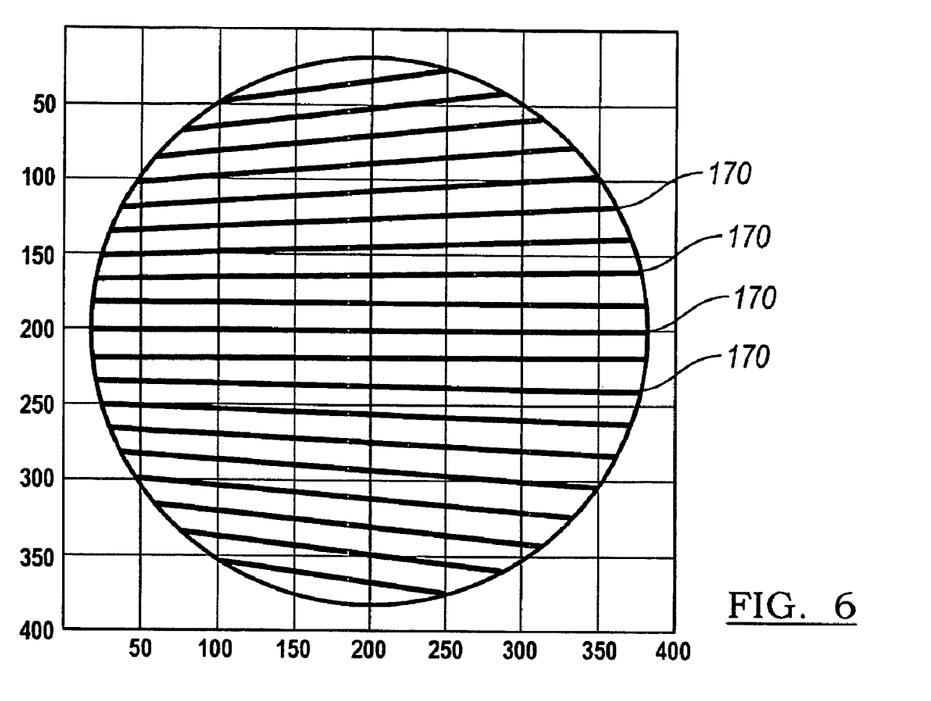
FIG. 6 is a view of x-ray projections illustrating the shift variant blur of a flat panel computed tomography system.

Reconstructed voxels were 0.2 mm and all data was noiseless for the purposes of spatial resolution investigation. This geometry resulted in a large, but manageable system matrix with approximately 300 million nonzero elements (only one quarter of these values had to be stored due to symmetry). Sample projection rays 170 are shown in FIG. 6 that illustrates the shift-variant nature of this particular geometry.

Figure 7:
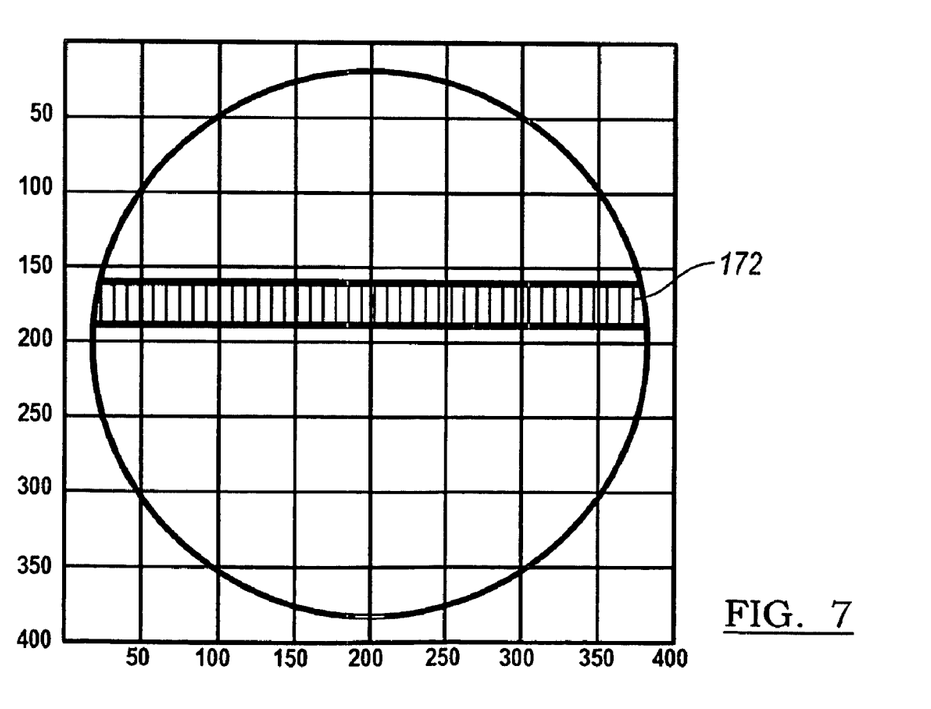
FIG. 7 is a view of the line pair phantom used to test the computed tomography system.

To investigate resolution properties of the model-based iterative approach versus traditional (pure ramp) filtered backprojection reconstruction (FBP), the line pair phantom 172, shown in FIG. 7 was used.

Figure 8:
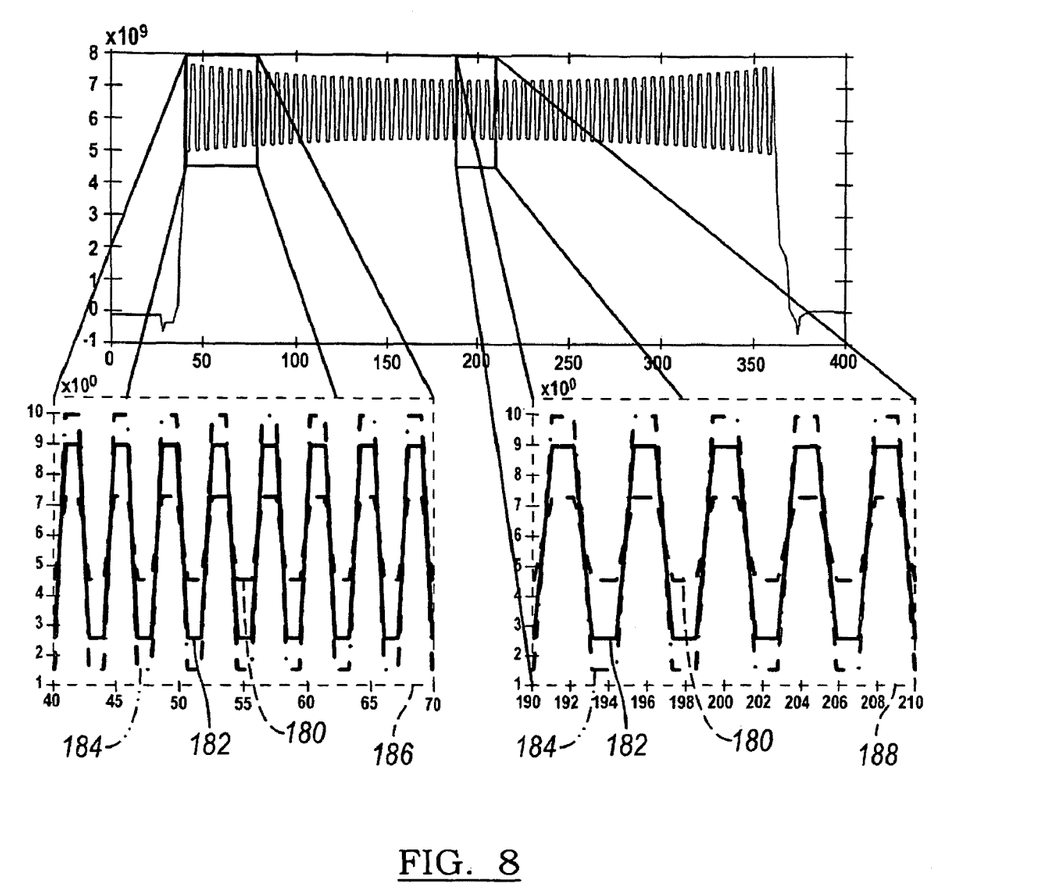
FIG. 8 is a view of results of the testing on the computed tomography system.

Results of reconstruction using the two methods 182 and 184 are compared to the actual values 180 in FIG. 8. The profiles 180, 182, and 184 are provided by looking at a single row through the line pairs (in particular, two zoomed regions 186 and 188). Note that the resolution is shift-variant and, therefore, the system resolution is generally better at the edges, as in region 186, than in the middle of the detector, 14 in region 188.

While the traditional (pure ramp) approach 182, which is a form of filtered backprojection, provides a reasonable reconstruction, the iterative approach 184 provides significantly better spatial resolution recovery.

Through accurate modeling of the combined source detector response function, resolution can be recovered that would ordinarily be lost using traditional approaches.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments of the present disclosure, the methods described herein may be implemented by software programs executable by a computer system. Further, in an exemplary, non-limited embodiment, implementations can include distributed processing, component/object distributed processing, and parallel processing. Alternatively, virtual computer system processing can be constructed to implement one or more of the methods or functionality as described herein.

Further the methods described herein may be embodied in a computer-readable medium. The term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

As a person skilled in the art will readily appreciate, the above description is meant as an illustration of the principles of this invention. This description is not intended to limit the scope or application of this invention in that the invention is susceptible to modification, variation and change, without departing from spirit of this invention, as defined in the following claims.

I claim:

1. A system for performing computed tomography, the system comprising:
    an x-ray source configured to project an x-ray beam toward a subject, wherein the x-ray source includes an anode having a target;
    a sensing array configured to receive the x-ray beam through the subject, to generate an image of the target area of the anode causing a shift variant blur of the x-ray beam received by the sensing array, the sensing array having a plurality of pixels; and
    a controller in communication with the sensing array to control and process acquisition by the sensing array, the controller being configured to adjust for the shift variant blur of the x-ray beam, wherein the controller generates a model of the shift variant blur corresponding to a pattern of contribution of each voxel based on an angle between the target and each pixel of the sensing array.

2. The system of claim 1, wherein the controller is configured to generate a matrix corresponding to the model.

3. The system of claim 2, wherein the controller is configured to process the image based on the matrix to adjust for the shift variant blur.

4. The system of claim 1, wherein the shift variant blur is modeled by the controller based on a location and orientation of the anode with respect to each pixel on the sensing array.

5. The system of claim 4, wherein the shift variant blur is modeled by the controller based on dimensions of the target.

6. A method for performing computed tomography, the method comprising the steps of:
    projecting an x-ray beam toward a subject using an anode having a target;
    receiving the x-ray beam through the subject to a sensing array to generate an image, wherein the target causes a shift variant blur of the x-ray beam received by the sensing array, the sensing array having a plurality of pixels;
    generating a model of the shift variant blur with a controller, said model corresponding to pattern of contribution of each voxel based on an angle between the target and each pixel of the sensing array; and
    adjusting for the shift variant blur of the x-ray beam, using the controller.

7. The method of claim 6, further comprising generating a matrix corresponding to the model.

8. The method of claim 7, further comprising processing the image based on the matrix to adjust for the shift variant blur.

9. The method of claim 6, further comprising modeling the shift variant blur based on a location and orientation of the target with respect to each pixel on the sensing array.

10. The method of claim 9, wherein the shift variant blur is modeled based on dimensions of the target.

11. The system of claim 1, wherein the model is generated based on the shift variant blur due to an apparent size of the target relative to a location and orientation of each pixel of the plurality of pixels.

12. The method of claim 6, wherein the model is generated based on the shift variant blur due to an apparent size of the target relative to a location and orientation of each pixel of the plurality of pixels.

13. A system for performing computed tomography, the system comprising:
    an x-ray source configured to project an x-ray beam toward a subject, wherein the x-ray source includes an anode having a target;
    a sensing array configured to receive the x-ray beam through the subject, to generate an image of the target of the anode causing a shift variant blur of the x-ray beam received by the sensing array, the sensing array having a plurality of pixels;
    a controller in communication with the sensing array to control and process acquisition by the sensing array, the controller being configured to adjust for the shift variant blur of the x-ray beam, wherein the controller generates a model of the shift variant blur due to the apparent size of the target based on the location and orientation of each pixel of the plurality of pixels.

* * * * *

UNITED STATES PATENT AND TRADEMARK OFFICE
CERTIFICATE OF CORRECTION

| | | |
|---|---|---|
| PATENT NO. | : 7,852,980 B2 | Page 1 of 1 |
| APPLICATION NO. | : 12/262600 | |
| DATED | : December 14, 2010 | |
| INVENTOR(S) | : Joseph W. Stayman | |

It is certified that error appears in the above-identified patent and that said Letters Patent is hereby corrected as shown below:

In the Claims

Claim 6, column 2, line 7, before "pattern" insert --a--.

Signed and Sealed this
Third Day of May, 2011

David J. Kappos
*Director of the United States Patent and Trademark Office*

UNITED STATES PATENT AND TRADEMARK OFFICE
CERTIFICATE OF CORRECTION

PATENT NO. : 7,852,980 B2  Page 1 of 1
APPLICATION NO. : 12/262600
DATED : December 14, 2010
INVENTOR(S) : Joseph W. Stayman It is certified that error appears in the above-identified patent and that said Letters Patent is hereby corrected as shown below:

In the Claims

Claim 6, column 8, line 7, before "pattern" insert --a--.

This certificate supersedes the Certificate of Correction issued May 3, 2011.

Signed and Sealed this
Thirty-first Day of May, 2011

David J. Kappos
*Director of the United States Patent and Trademark Office*